US009364185B2

(12) United States Patent
Strickland (10) Patent No.: US 9,364,185 B2
(45) Date of Patent: Jun. 14, 2016

(54) LOW ENERGY WIRELESS COMMUNICATION SYSTEMS AND METHODS FOR MEDICAL DEVICES

(71) Applicant: Roche Diagnostics Operations, Inc., Indianapolis, IN (US)

(72) Inventor: Raymond A. Strickland, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 348 days.

(21) Appl. No.: 14/155,954

(22) Filed: Jan. 15, 2014

(65) Prior Publication Data

US 2015/0196258 A1 Jul. 16, 2015

(51) Int. Cl.
*A61B 5/00* (2006.01)
*H04W 4/00* (2009.01)
*H04L 1/00* (2006.01)

(52) U.S. Cl.
CPC ............... *A61B 5/74* (2013.01); *H04L 1/0007* (2013.01); *H04L 1/0061* (2013.01); *H04W 4/005* (2013.01); *H04W 4/008* (2013.01)

(58) Field of Classification Search
None
See application file for complete search history.

(56) References Cited

U.S. PATENT DOCUMENTS

| 2007/0186130 | A1* | 8/2007 | Holm | H04L 1/0041 714/701 |
| 2010/0302979 | A1* | 12/2010 | Reunamaki | H04M 1/7253 370/311 |
| 2012/0096451 | A1 | 4/2012 | Tenbarge et al. | |
| 2012/0266251 | A1* | 10/2012 | Birtwhistle | G06F 19/323 726/26 |

OTHER PUBLICATIONS

Specification of the Bluetooth System—Specification vol. 0, "Master Table of Contents & Compliance Requirements," Covered Core Package version 4.0; Current Master TOC; Jun. 30, 2010; 2302 Pages.
ISO/IEEE 11073 Personal Health Data (PHD) Standards—Wikipedia; Oct. 31, 2013, XP055172590, Retrieved from the Internet: URL:http://en.wikipedia.org/w/index.php?title=ISO/IEE 1107 3 Personal Health Data (PHD) Standards&oldid=579637377, pp. 1-4 and 7-10.
IEEE 11073 Software Development Kit for Agent Devices IAPS11073; Nov. 30, 2011, XP055172588 Retrieved from the Internet: URL:http://www.stellmann.de/fileadmin/01_Copntent/pdf/IEE_Agent_SDK_en_ro5.pdf.
ISO/IEEE 11073-20601 Implementation Using Official Android HDP API (ICS 4.0.3); Mar. 1, 2012 XP054975758; Retrieved from the Internet: URL:https://www.youtube.com/watch?v=xiXCSMdYXUg.

* cited by examiner

*Primary Examiner* — Thai Nguyen
(74) *Attorney, Agent, or Firm* — Harness, Dickey (57) ABSTRACT

A method performed by a medical device for transmitting data packets includes: removing select data fields from a data packet defined in accordance with IEEE standard 11073 to form a modified data packet; determining a length of the modified data packet; determining whether the length of the modified data packet is greater than a predetermined maximum length of data packets under the Bluetooth low energy protocol, as defined in Bluetooth Core Specification version 4.0 or higher; when the length of the modified data packet is greater than the predetermined maximum length of data packets defined under the Bluetooth low energy protocol, partitioning the modified data packet into a plurality of individual data packets, wherein each of the individual data packets includes a portion of the modified data packet; and transmitting the individual data packets via an antenna in accordance with the Bluetooth low energy protocol.

19 Claims, 7 Drawing Sheets

FIG. 8

LOW ENERGY WIRELESS COMMUNICATION SYSTEMS AND METHODS FOR MEDICAL DEVICES

FIELD

The present disclosure relates to handheld medical devices and more particularly to systems and methods for reducing wireless communication overhead of medical devices.

BACKGROUND

Persons with diabetes have difficulty regulating blood glucose levels in their bodies. As a consequence, many of these persons carry specialized electronic meters, called blood glucose meters, which allow them to periodically measure their glucose levels and take appropriate action, such as administering insulin. These persons may also carry with them a portable communication device, such as a mobile phone, a personal digital assistant, a tablet or similar device. People often rely on their portable communication device as the primary means for planning, scheduling and communicating with others. As a result, most portable communication devices are equipped with sophisticated software which provides user-friendly means for viewing and inputting data. Accordingly, a person with diabetes may wish to wirelessly transmit the results of a blood glucose measurement from their glucose meter to their portable communication device in order, for example, to display, analyze or report on the data.

Handheld diabetes management devices include one or more batteries that can provide power. For example, some handheld diabetes management devices include standard size batteries, and some handheld diabetes management devices include a non-standard sized, re-chargeable battery. Handheld medical devices may communicate wirelessly. However, wireless communication may consume battery power. There is therefore a need for handheld medical devices to communicate wirelessly while minimizing power consumption.

The background description provided herein is for the purpose of generally presenting the context of the disclosure. Work of the presently named inventors, to the extent it is described in this background section, as well as aspects of the description that cannot otherwise qualify as prior art at the time of filing, are neither expressly nor impliedly admitted as prior art against the present disclosure.

SUMMARY

A medical device for transmitting data packets using a communication protocol defined in accordance with the Bluetooth low energy protocol is disclosed. The medical device includes: a processor module that removes select data fields from a data packet defined in accordance with IEEE standard 11073 to form a modified data packet, that determines a length of the modified data packet and that, when the length of the modified data packet is greater than a predetermined maximum length of data packets under the Bluetooth low energy protocol as defined in Bluetooth Core Specification version 4.0 or higher, partitions the modified data packet into a plurality of individual data packets, where each of the individual data packets includes a portion of the modified data packet; and a transceiver that transmits the individual data packets via an antenna in accordance with the Bluetooth low energy protocol.

A method performed by a medical device for transmitting data packets using a communication protocol defined in accordance with the Bluetooth low energy protocol is described. The method includes: removing a header field and at least one other data field from a data packet defined in accordance with IEEE standard 11073-20601 to form a modified data packet, the data packet including one of: code for commanding another medical device to perform a function; one or more measurements taken by the medical device; and code for a response to a command received from another medical device. The method further includes: leaving data from other, non-removed fields of the data packet defined in accordance with IEEE standard 11073-20601 unchanged to form the modified data packet; determining a length of the modified data packet; determining whether the length of the modified data packet is greater than a predetermined maximum length of data packets under the Bluetooth low energy protocol, as defined in Bluetooth Core Specification version 4.0 or higher; determining a total number of individual data packets based on the length of the modified data packet and the predetermined maximum length of data packets; when the length of the modified data packet is greater than the predetermined maximum length of data packets defined under the Bluetooth low energy protocol, partitioning the modified data packet into N individual data packets, wherein each of the N individual data packets includes a portion of the modified data packet and N is equal to the total number of individual data packets; and transmitting the N individual data packets via an antenna in accordance with the Bluetooth low energy protocol.

A method performed by a medical device for transmitting data packets using a communication protocol defined in accordance with the Bluetooth low energy protocol is disclosed. The method includes: removing select data fields from a data packet defined in accordance with IEEE standard 11073 to form a modified data packet; determining a length of the modified data packet; determining whether the length of the modified data packet is greater than a predetermined maximum length of data packets under the Bluetooth low energy protocol, as defined in Bluetooth Core Specification version 4.0 or higher; when the length of the modified data packet is greater than the predetermined maximum length of data packets defined under the Bluetooth low energy protocol, partitioning the modified data packet into a plurality of individual data packets, wherein each of the individual data packets includes a portion of the modified data packet; and transmitting the individual data packets via an antenna in accordance with the Bluetooth low energy protocol.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

Figure 1:
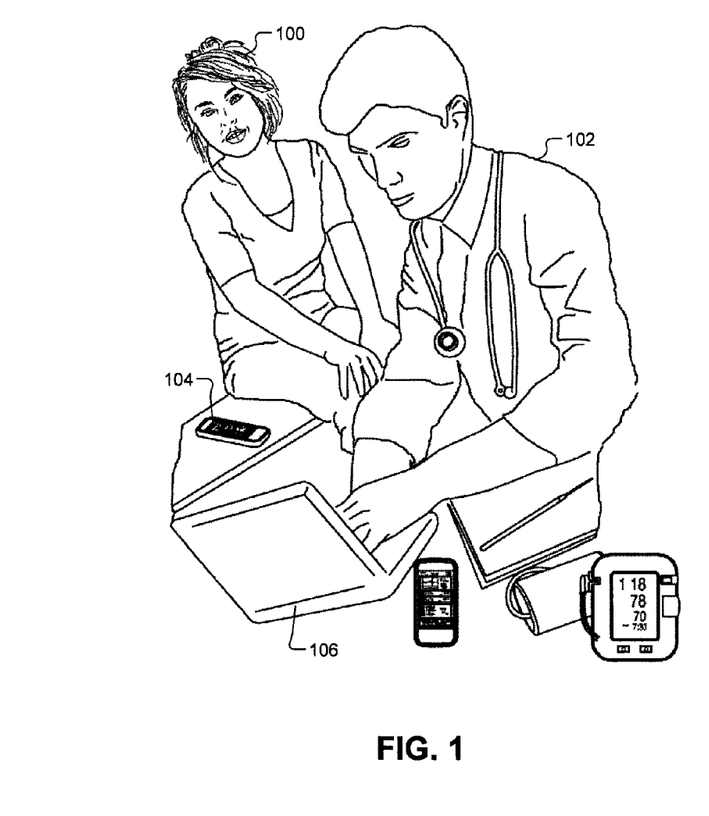
FIG. 1 shows a patient and a health care professional along with various devices that can be used to help the patient monitor and control health.

Referring now to FIG. 1, a patient 100 with diabetes and a health care professional 102 are shown in a clinical environment. The patient 100 with diabetes can be diagnosed with a metabolic syndrome, pre-diabetes, type 1 diabetes, type 2 diabetes, gestational diabetes, etc. Healthcare providers for diabetes are diverse and include nurses, nurse practitioners, physicians, endocrinologists, and others and are collectively referred to as health care professionals.

During a health care consultation, the patient 100 typically shares with the health care professional 102 a variety of data including blood glucose (bG) measurements, continuous glucose monitor data, amounts and type of insulin administered, amounts of food and beverages consumed, exercise schedules, health status, and other lifestyle information. The health care professional 102 can obtain additional data for the patient 100, such as measurements of HbA1C, cholesterol levels, plasma glucose, triglycerides, blood pressure, and weight. The data can be recorded manually or electronically on a handheld diabetes management device 104 (e.g., a handheld bG monitor device), a diabetes analysis software executed on a personal computer (PC) 106, and/or a web-based diabetes analysis site.

The health care professional 102 can analyze the patient data manually or electronically using the diabetes analysis software and/or the web-based diabetes analysis site. After analyzing the data and reviewing how efficacious previously prescribed therapy is and how well the patient 100 followed the previously prescribed therapy, the health care professional 102 can decide whether to modify a therapy prescribed for the patient 100.

Figure 2:
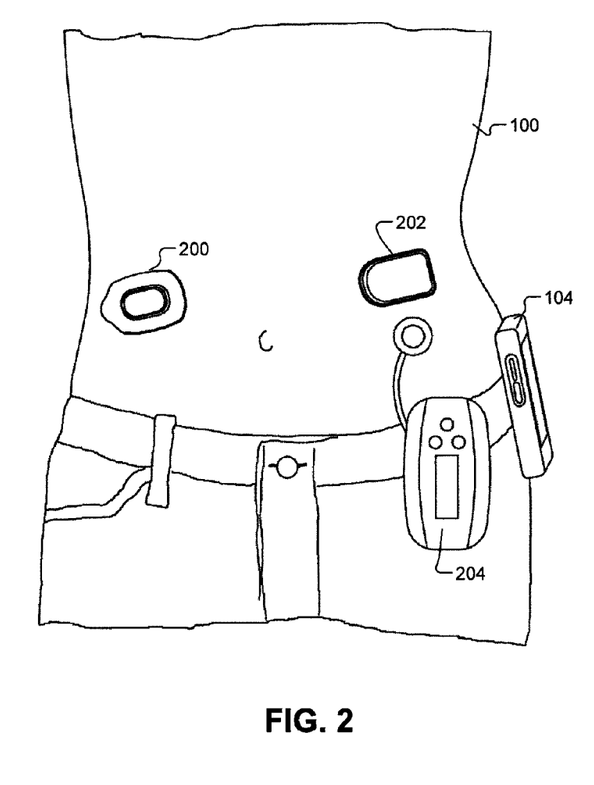
FIG. 2 shows a patient with a continuous glucose monitor (CGM), an ambulatory durable insulin infusion pump, an ambulatory non-durable insulin infusion pump, and a blood glucose (bG) management device.

Referring now to FIG. 2, the patient 100 can use a continuous glucose monitor (CGM) 200, an ambulatory durable insulin infusion pump 204 or an ambulatory non-durable insulin infusion pump 202, and the diabetes management device 104. The CGM 200 can use a subcutaneous sensor to sense and monitor the amount of glucose (e.g., glucose concentration) of the patient 100. The CGM 200 communicates glucose measurements to the diabetes management device 104.

The diabetes management device 104 performs various tasks including measuring and recording bG measurements, determining an amount of insulin to be administered to the patient 100 via the insulin pump 202 or 204, receiving user input via a user interface, archiving data, performing structured bG tests, etc. The diabetes management device 104 can wirelessly transmit commands to the insulin pump 202 or 204, and the insulin pump 202 or 204 selectively delivers insulin to the patient 100 accordingly. Insulin can be delivered in the form of a meal bolus dose, a correction bolus dose, a basal dose, etc.

Figure 3:
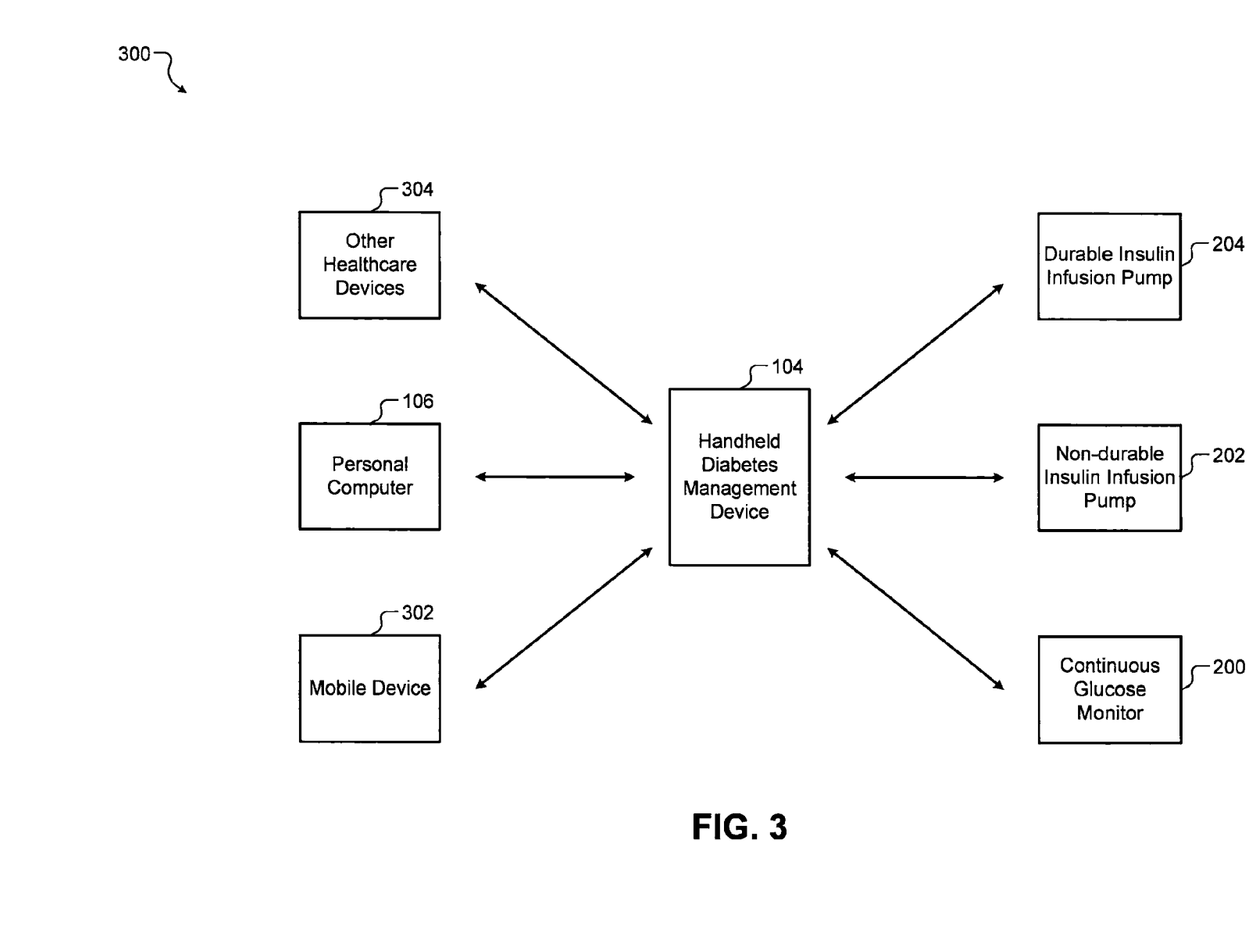
FIG. 3 shows a diabetes care system of systems that can be used to manage diabetes.

Referring now to FIG. 3, a diabetes management system 300 is shown which can be used by the patient 100 and/or the health care professional 102. The system 300 can include one or more of the following devices: the diabetes management device 104, the CGM 200, the insulin pump 202 or 204, a mobile device 302, the diabetes management software (DMS) executed on the computer 106, and one or more other health care devices 304. The diabetes management device 104 can be configured as a system "hub" and communicate with one or more of the other devices of the system 300. The insulin pump 202 or 204, the mobile device 302, or another suitable device can alternatively serve as the system hub.

Communication between various devices in the system 300 can be performed using wireless interfaces (e.g., Bluetooth) and/or wired interfaces (e.g., USB). Communication protocols used by these devices can include protocols compliant with the IEEE 11073 standard as extended using guidelines provided by Continua Health Alliance Design Guidelines. Further, health care records systems such as Microsoft HealthVault and Google Health can be used by the patient 100 and the health care professional 102 to exchange information.

Figure 4:
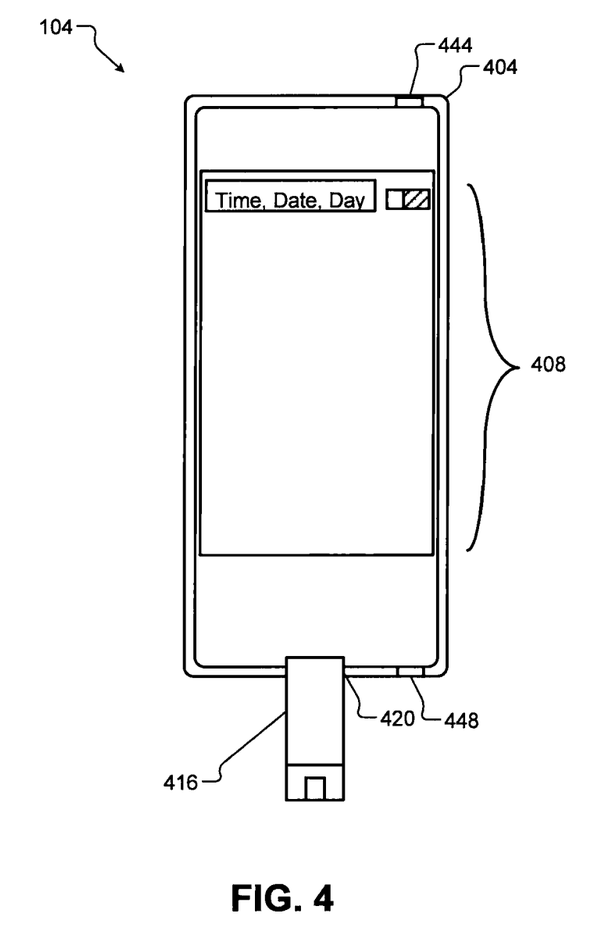
FIG. 4 is a front view of an example implementation of a handheld diabetes management device.

Referring now to FIG. 4, a high level illustration of an example embodiment of the diabetes management device 104 is presented. The diabetes management device 104 includes, among other things, a housing 404, user unit control switches (not specifically numbered), a touchscreen display 408, and a bG test strip port 420. The user unit control switches, for example, can include ON/OFF switches, volume switches, alarm switches for bG testing and/or insulin administration, and/or one or more other switches or other types of control devices that a patient can use to control functions/operations of the diabetes management device 104.

A blood sample can be added to a bG test strip 416, and the bG test strip 416 can be inserted into the bG test strip port 420. The bG test strip 416 can be inserted into the bG test strip port 420 by a patient, from a test strip drum (not shown) located within the housing 404, or in another suitable manner. The bG test strip 416 is shown already inserted into the bG test strip port 420 in the example of FIG. 4.

Although the display 408 is described herein as a touchscreen display, the diabetes management device 104 can include another suitable type of display (e.g., LED, LCD, etc.). If a touchscreen display is not used, the user control switches can include specific buttons or controls by which a user is able to select various options and execute various functions of the diabetes management device 104. The diabetes management device 104 may include one or more visual indicators, such as LED 444. The diabetes management device 104 may include one or more audio output devices, such as speaker 448.

Figure 5:
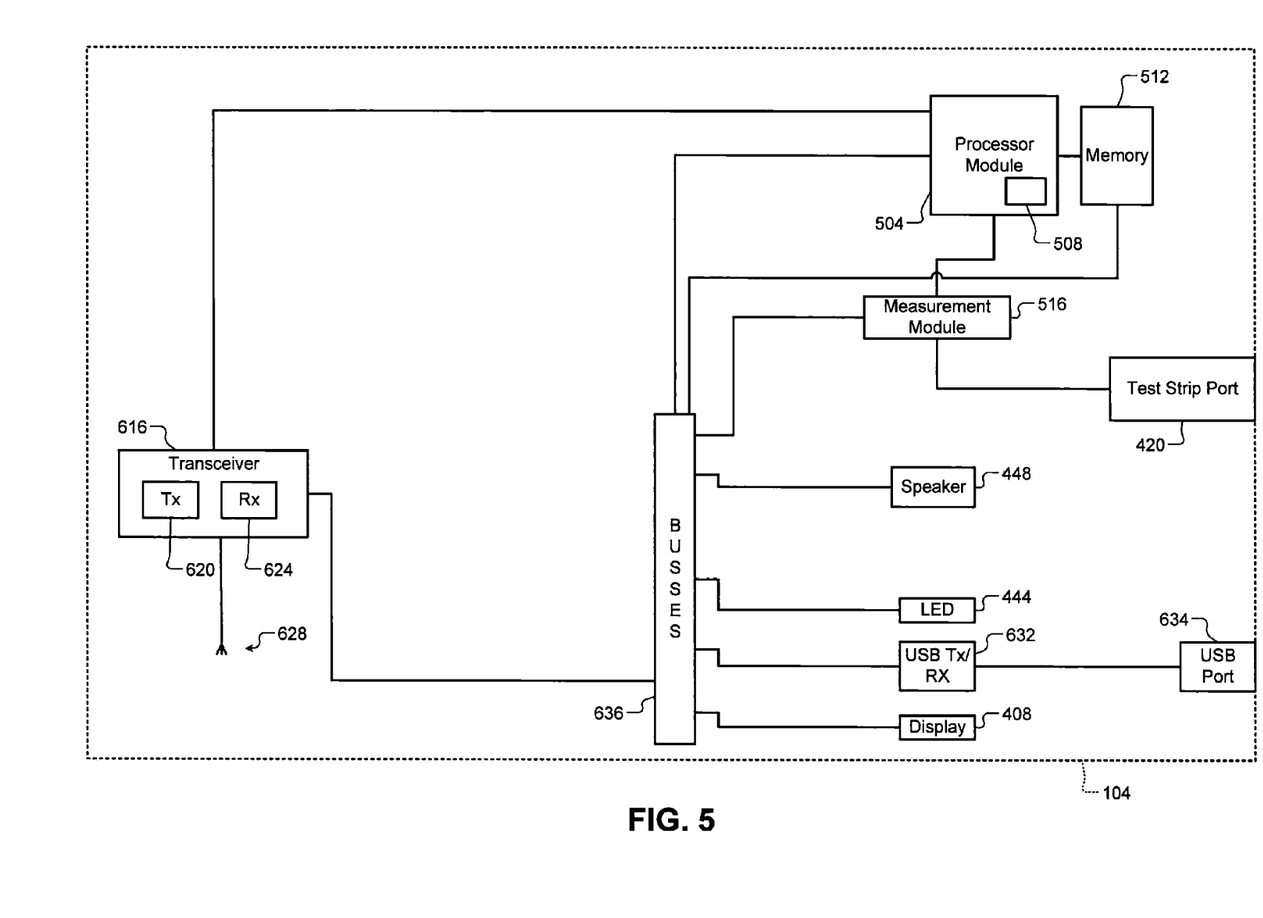
FIG. 5 is a functional block diagram of an example diabetes management device.

FIG. 5 includes a functional block diagram of an example implementation of the diabetes management device 104. The diabetes management device 104 includes a processor module 504 that includes a processor 508. Code for executing the functionality of the diabetes management device 104 is stored in memory 512. While the memory 512 is shown as being external to the processor module 504, the memory 512 may be wholly or partially integrated within the processor module 504.

The diabetes management device 104 includes a measurement module 516. The measurement module 516 measures one or more characteristics of a sample of a bodily fluid. For example, the measurement module 516 measures bG of a sample of blood present on a bG test strip that is inserted into the bG test strip port 420. The measurement module 516 may generate sample data based on the characteristics of the sample and provide the sample data to the processor module

504. The processor module 504 may store the sample data and other data (e.g., user input data and other types of data) in the memory 512.

The diabetes management device 104 also includes components for communicating between the diabetes management device 104 and one or more other devices. For example, the diabetes management device 104 includes wireless data transceiver 616 for wirelessly communicating with other devices, such as the CGM 200, the mobile device 302, the computer 106, the insulin pump 202, and/or the insulin pump 204.

The transceiver 616 includes a transmitter (Tx) 620 and a receiver (Rx) 624. The transceiver 616 receives and transmits signals wirelessly via one or more antennas, such as antenna 628. The transceiver 616 may transmit and receive, for example, commands, responses to commands, and object data (e.g., sample data) wirelessly.

The diabetes management device 104 may also include one or more other wireless and/or wired data transceivers. For example, the diabetes management device 104 may include a universal serial bus (USB) transceiver 632 and/or one or more other suitable types of data transceivers. The USB transceiver 632 may transmit and receive signals via a USB port 634. The transceiver 616, the processor module 504, the measurement module 516, the USB transceiver 632, and other components may be connected to one or more data busses 636.

Commands received by the diabetes management device 104 are executable by the processor module 504. Commands transmitted by the diabetes management device 104 are executable by another device. Responses to commands received by the diabetes management device 104 indicate a response of another device (e.g., a CGM, a durable insulin delivery device, or a non-durable insulin delivery device) to a command transmitted to that device by the diabetes management device 104. Responses to commands that are transmitted by the diabetes management device 104 are generated by the diabetes management device in response to the receipt of a command by the diabetes management device 104 issued by another device (e.g., a CGM, a durable insulin delivery device, or a non-durable insulin delivery device). Code for commands and responses to commands is stored in the memory 512.

Object data is readable and can be written by the processor module 504. The diabetes management device 104 can receive object data from other devices and can transmit object data stored in the memory 512 to other devices. Object data is also stored in the memory 512.

To transmit a command, a response to a command, or object data to another device, the diabetes management device 104 packetizes the code and/or data to be transmitted. For example, the processor module 504 generates a data packet in accordance with IEEE standard 11073 (e.g., IEEE standard 11073-20601) to communicate the code for a command, a response to a command, or object data to another device. The data packet could be transmitted wirelessly. A device receiving the data packet could parse the data packet to obtain the command, response, or object data from the received data packet for use.

Data packets defined in accordance with IEEE standard 11073, however, may be large. Transmitting and receiving data packets defined in accordance with IEEE standard 11073 may therefore consume more energy than other forms of wireless communication, such as the Bluetooth Low Energy (BLE) standard defined within the Bluetooth Core Specification version 4.0 or higher.

Figure 6:
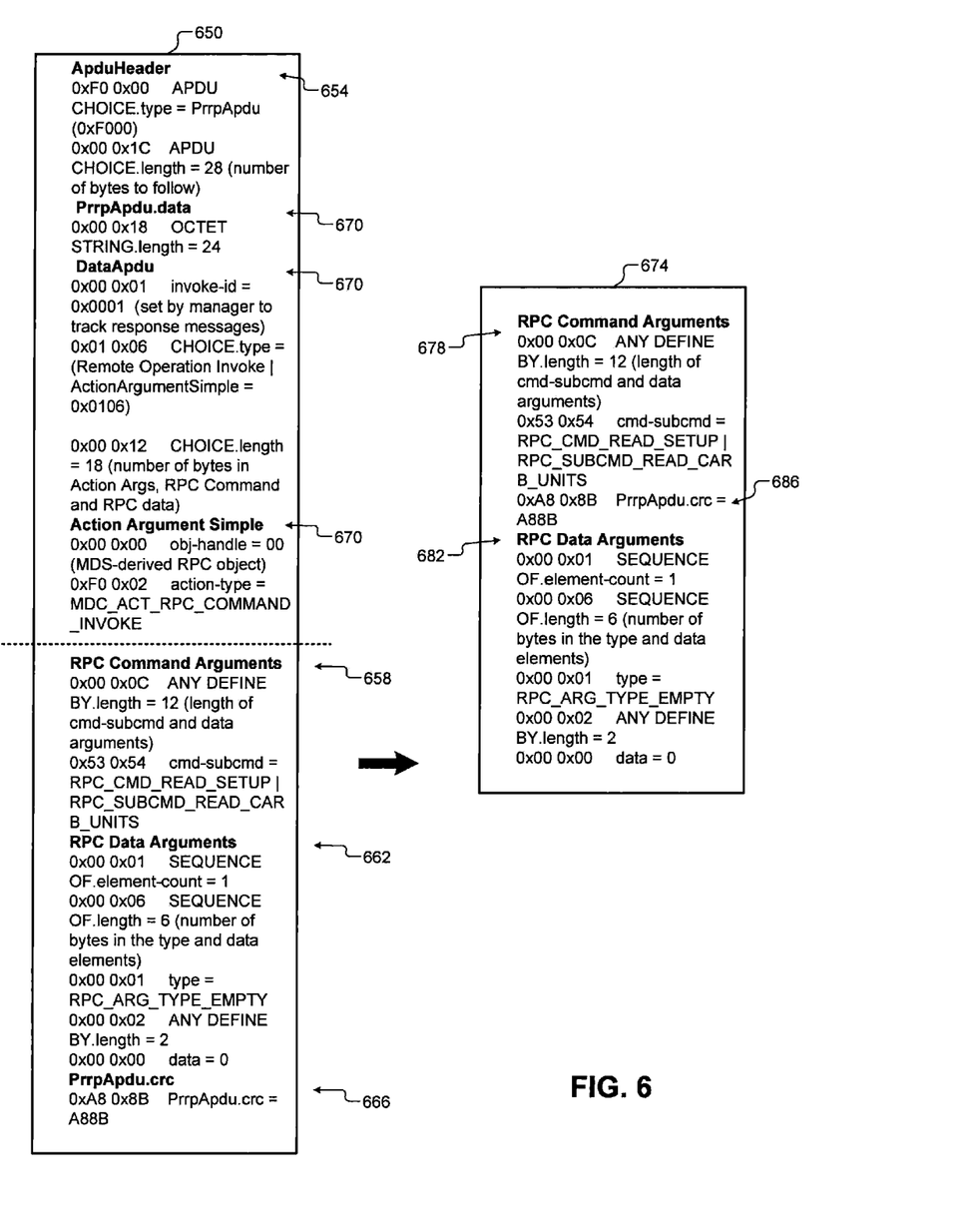
FIG. 6 includes example illustrations of a data packet defined in accordance with IEEE standard 11073 and a modified data packet formed from the data packet.

FIG. 6 includes an example data packet 650 for a command that is defined in accordance with IEEE standard 11073. While the example of a data packet for a command is shown, data packets for communicating responses to commands and object data have similar structures and are defined in accordance with IEEE standard 11073.

The data packet 650 includes a plurality of fields, such as a header field 654, a command arguments field 658, a data arguments field 662, a cyclical redundancy check (CRC) field 666, and other fields, collectively indicated by 670, in accordance with IEEE standard 11073. The command arguments field 658 includes the command and may include one or more sub-commands. The command arguments field 658 may also include a length of the command and one or more sub-commands, if any.

The data arguments field 662 includes a sequence number of the data packet 650 out of a total number of data packets used to convey the command and one or more sub-commands. The data arguments field 662 also includes a type and a length. The CRC field 666 includes data for performing a CRC to verify correct transmission and receipt of the data packet. While CRC is shown and discussed, another suitable type of error detecting code may be used.

The processor module 504 removes various fields from data packets defined in accordance with IEEE standard 11073 to form modified data packets for transmission according to the BLE (Bluetooth Low Energy) standard as defined in Bluetooth Core Specification version 4.0 or higher. For example, referring to the example of FIG. 6, the processor module 504 may remove the header field 654 and the other fields 670 from the data packet 650 to produce a modified data packet. FIG. 6 includes an example modified data packet 674 formed based on the example data packet 650.

The modified data packet 674 includes a plurality of fields including a command arguments field 678 and a data arguments field 682. The command arguments field 678 includes data that is identical to the data in the command arguments field 658. The data arguments field 682 includes data that is identical to the data in the data arguments field 662. The sequence number of the modified data packet 674 and/or the total number of data packets used may be different than that of the data packet 650, as discussed further below. The processor module 504 may also remove the CRC field 666, calculate a new CRC value based on the modified data packet 674, and store the new CRC value in a CRC field 686 in the modified data packet 674.

For each modified data packet to be transmitted, the processor module 504 determines a length of that modified data packet and compares the length of the modified data packet to a predetermined maximum data packet length. The predetermined maximum data packet length is defined by the BLE standard as defined in Bluetooth Core Specification version 4.0 or higher. For example, the predetermined maximum data packet length may be approximately 20 bytes or another suitable length. If the length of the modified data packet is less than the predetermined maximum length, the transceiver 616 may transmit the modified data packet.

Figure 7:
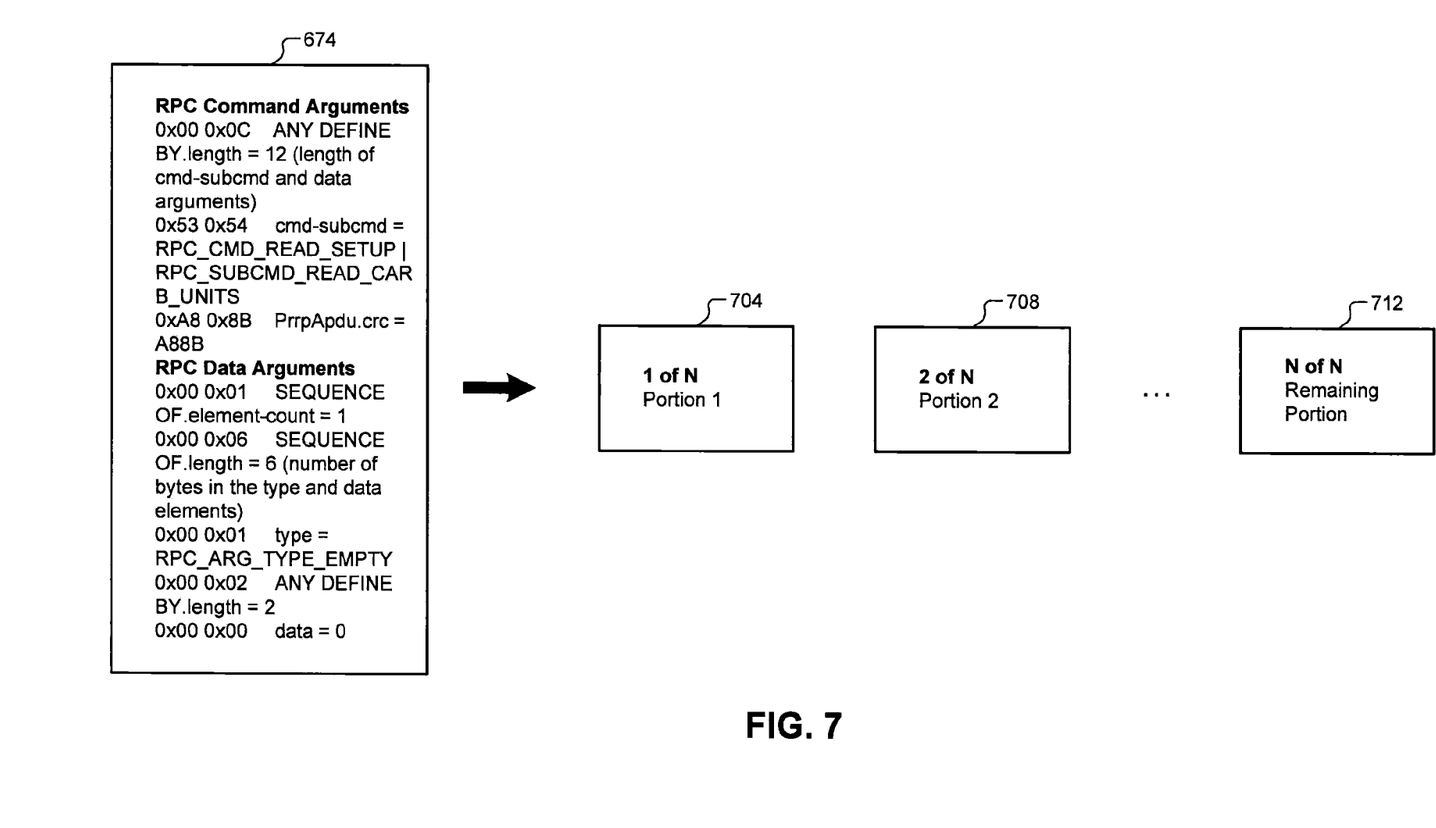
FIG. 7 includes a modified data packet and a plurality of individual packets resulting from partitioning of a modified data packet.

If the length of the modified data packet is greater than the predetermined maximum length, the processor module 504 partitions the modified data packet into a plurality of individual packets for transmission. FIG. 7 includes an example illustration of the example modified data packet 674 and N individual data packets 704, 708, and 712 resulting from partitioning of the modified data packet 674. While three individual data packets are shown in FIG. 7, N is an integer greater than or equal to 2.

The processor module 504 may determine a number of individual data packets necessary to transmit the data of the modified data packet based on the length of the modified data packet 674 and the predetermined maximum length of data packets under the BLE standard. For example, the processor module 504 may determine the number of individual data packets necessary by dividing the length of the modified data packet by the predetermined maximum length and rounding the result up to a nearest integer.

The processor module 504 includes a portion of the modified data packet 674 in each of the individual data packets. For example, the individual data packet 704 includes a first portion of the modified data packet 674, the individual data packet 708 includes a second portion of the modified data packet 674, and the individual data packet 712 includes a remainder of the modified data packet.

In each of the individual data packets, the processor module 504 also includes a transmission order indicator and an indicator of a total number of individual data packets used to together transmit the modified data packet. For example, the individual data packet 704 includes data indicating that it is the first of the N individual data packets, the individual data packet 708 includes data indicating that it is the second of the N individual data packets, and the individual data packet 712 includes data indicating that it is the N-th one of the N individual data packets.

The transceiver 616 transmits the individual data packets in the order indicated by the transmission order indicators. For example, the transceiver 616 transmits the individual data packet 704 first, the individual data packet 708 second, . . . and the individual data packet 712 N-th. The transceiver 616 transmits the individual data packets wirelessly using the BLE standard defined in accordance with the Bluetooth Core Specification version 4.0 or higher.

Based on the transmission order indicators, a device receiving the individual data packets can assemble the individual data packets in the proper order to re-form the modified data packet. The device receiving the individual data packets can also verify the correctness of the re-formed modified data packet using the CRC data stored in the re-formed modified data packet. The device can then act based on the data stored in the re-formed modified data packet.

While the transmission using the diabetes management device 104 is shown and discussed, the present application is also applicable to other types of medical devices and partially implantable medical devices including, but not limited to, personal computers executing medical functions, handheld triglyceride management devices, handheld cholesterol management devices, handheld coagulation management devices, handheld analyte management devices, continuous glucose monitors, and insulin pumps. Additionally, modifying data packets defined in accordance with IEEE standard 11073 to produce modified data packets for communication in accordance with the Bluetooth Core Specification version 4.0 or higher, the present application is also applicable to modifying data packets defined in accordance with another suitable standard to produce modified data packets for communication in accordance with another suitable wireless data transmission standard.

Figure 8:
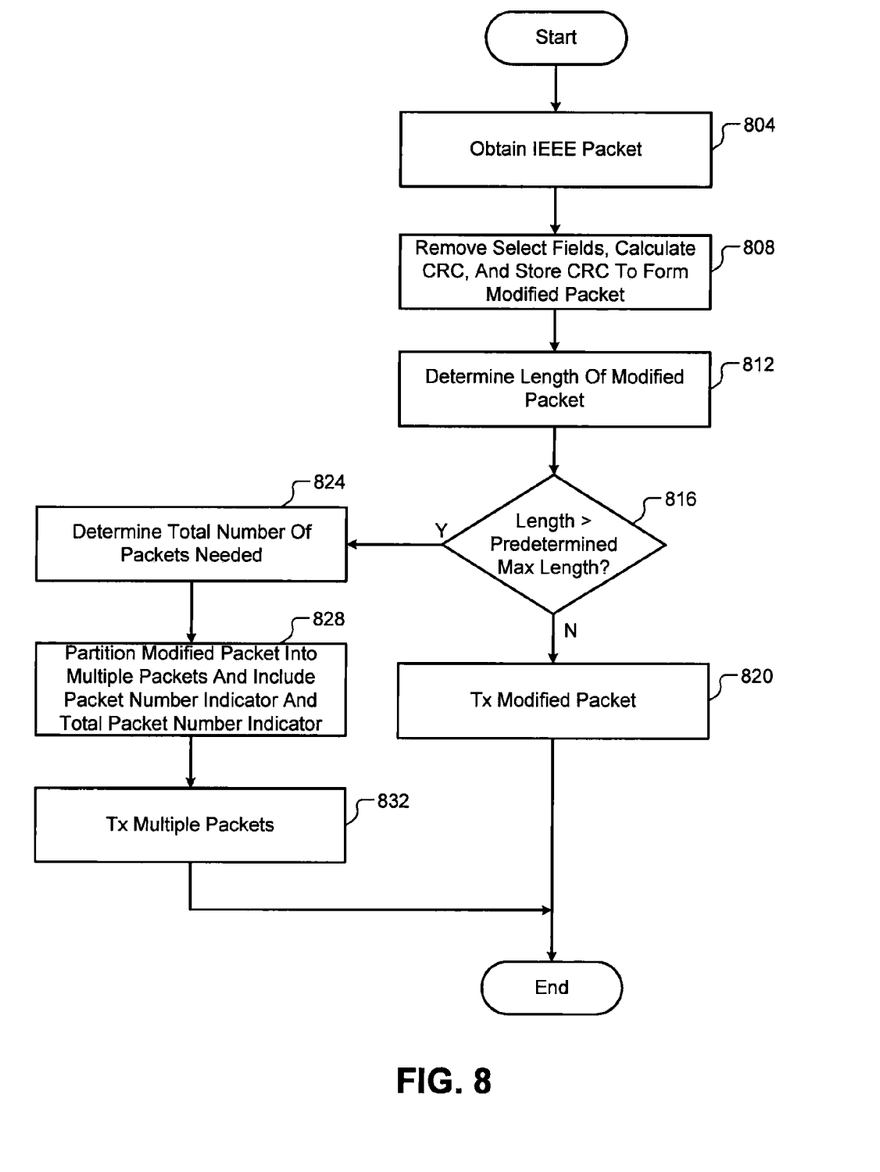
FIG. 8 includes a flowchart depicting an example method of transmitting data packets in accordance with the Bluetooth Low Energy (BLE) standard, as defined in Bluetooth Core Specification version 4.0 or higher.

FIG. 8 is a flowchart depicting an example method of transmitting data packets in accordance with the BLE standard, as defined in Bluetooth Core Specification version 4.0 or higher. Control may begin with 804 where the processor module 504 obtains a data packet defined in accordance with IEEE standard 11073, such as IEEE standard 11073-20601.

At 808, the processor module 504 removes select fields from the data packet defined in accordance with IEEE standard 11073 to form a modified data packet. For example, the processor module 504 may remove the header field and other fields from the data packet to produce a modified data packet.

The processor module 504 may also remove the CRC field from the data packet defined in accordance with IEEE standard 11073. The processor module 504 may calculate a new CRC value based on the modified data packet and stored the new CRC value in the modified data packet at 808.

The processor module 504 determines a length of the modified data packet at 812. At 816, the processor module 504 compares the length of the modified data packet to the predetermined maximum data packet length defined by the BLE standard, as defined in Bluetooth Core Specification version 4.0 or higher. For example, the processor module 504 may determine whether the length of the modified data packet is greater than the predetermined maximum data packet length at 816.

If the length of the modified data packet is less than the predetermined maximum length, the transceiver 616 may transmit the modified data packet at 820, and control may end. If the length of the modified data packet is greater than the predetermined maximum length, control may continue with 824.

At 824, the processor module 504 may determine a number of individual packets needed to transmit the modified data packet. For example, the processor module 504 may determine the number of individual data packets needed to transmit the modified data packet by dividing the length of the modified data packet by the predetermined maximum length and rounding the result up to the nearest integer.

At 828, the processor module 504 partitions the modified data packet into the number of individual data packets. The processor module 504 also includes the transmission order indicator and the total number of packets used to transmit the modified data packet in each of the individual data packets at 828. At 832, the transceiver 616 transmits the individual data packets in the order of the transmission order indicators in accordance with the BLE standard as defined in the Bluetooth Core Specification version 4.0 or higher.

Based on the transmission order indicators, a device receiving the individual data packets can assemble the individual data packets in the proper order to re-form the modified data packet. The device receiving the individual data packets can also verify the correctness of the re-formed modified data packet using the CRC data stored in the re-formed modified data packet. The device can then act based on the data stored in the re-formed modified data packet.

In a feature, a method performed by a medical device for transmitting data packets using a communication protocol defined in accordance with the Bluetooth low energy protocol is disclosed. The method includes: removing select data fields from a data packet defined in accordance with IEEE standard 11073 to form a modified data packet; determining a length of the modified data packet; determining whether the length of the modified data packet is greater than a predetermined maximum length of data packets under the Bluetooth low energy protocol, as defined in Bluetooth Core Specification version 4.0 or higher; when the length of the modified data packet is greater than the predetermined maximum length of data packets defined under the Bluetooth low energy protocol, partitioning the modified data packet into a plurality of individual data packets, wherein each of the individual data packets includes a portion of the modified data packet; and transmitting the individual data packets via an antenna in accordance with the Bluetooth low energy protocol.

In further features, the select data fields includes a header field.

In still further features, the IEEE standard 11073 is IEEE standard 11073-20601.

In yet further fields, removing select data fields from the data packet defined in accordance with IEEE standard 11073 includes removing a data field that includes error detecting code data.

In further features, the method further includes: calculating new error correcting code data after the removal of the select data fields; and storing the new error correcting code data in the modified data packet.

In still further features, the error detecting code data includes data for a cyclical redundancy check.

In yet further features, the method further includes: determining a total number of individual data packets based on the length of the modified data packet and the predetermined maximum length of data packets defined under the Bluetooth low energy protocol; and partitioning the modified data packet into the total number of individual data packets.

In further features, the method further includes determining the total number of individual data packets by dividing the length of the modified packet by the predetermined maximum length and rounding the result up to the nearest integer.

In still further features, partitioning the modified data packet further includes appending each of the plurality of individual data packets with an indicator of the total number of individual data packets and a transmission order indicator.

In yet further features, the method further includes leaving data from other, non-removed fields of the data packet defined in accordance with IEEE standard 11073 unchanged to form the modified data packet.

In further features, the data packet includes code for commanding another medical device to perform a function.

In still further features, the data packet includes one or more measurements taken by the medical device.

In yet further features, the data packet includes code for a response to a command received from another medical device.

In further features, the method further includes, when the length of the modified data packet is less than the predetermined maximum length of data packets under the Bluetooth low energy protocol, transmitting the modified data packet.

In a feature, a method performed by a medical device for transmitting data packets using a communication protocol defined in accordance with the Bluetooth low energy protocol is described. The method includes: removing a header field and at least one other data field from a data packet defined in accordance with IEEE standard 11073-20601 to form a modified data packet, the data packet including one of: code for commanding another medical device to perform a function; one or more measurements taken by the medical device; and code for a response to a command received from another medical device. The method further includes: leaving data from other, non-removed fields of the data packet defined in accordance with IEEE standard 11073-20601 unchanged to form the modified data packet; determining a length of the modified data packet; determining whether the length of the modified data packet is greater than a predetermined maximum length of data packets under the Bluetooth low energy protocol, as defined in Bluetooth Core Specification version 4.0 or higher; determining a total number of individual data packets based on the length of the modified data packet and the predetermined maximum length of data packets; when the length of the modified data packet is greater than the predetermined maximum length of data packets defined under the Bluetooth low energy protocol, partitioning the modified data packet into N individual data packets, wherein each of the N individual data packets includes a portion of the modified data packet and N is equal to the total number of individual data packets; and transmitting the N individual data packets via an antenna in accordance with the Bluetooth low energy protocol.

In still further features, removing at least one other data field from the data packet defined in accordance with IEEE standard 11073-20601 includes removing a data field that includes error detecting code data, and the method further includes: calculating new error correcting code data after the removal of the header field and the at least one other data field; and storing the new error correcting code data in the modified data packet.

In yet further features, the error detecting code data includes data for a cyclical redundancy check.

In further features, the method further includes determining the total number of individual data packets by dividing the length of the modified packet by the predetermined maximum length and rounding the result up to the nearest integer.

In still further features, partitioning the modified data packet further comprises appending each of the plurality of individual data packets with an indicator of the total number of individual data packets and a transmission order indicator.

In a feature, a medical device for transmitting data packets using a communication protocol defined in accordance with the Bluetooth low energy protocol is disclosed. The medical device includes: a processor module that removes select data fields from a data packet defined in accordance with IEEE standard 11073 to form a modified data packet, that determines a length of the modified data packet and that, when the length of the modified data packet is greater than a predetermined maximum length of data packets under the Bluetooth low energy protocol as defined in Bluetooth Core Specification version 4.0 or higher, partitions the modified data packet into a plurality of individual data packets, where each of the individual data packets includes a portion of the modified data packet; and a transceiver that transmits the individual data packets via an antenna in accordance with the Bluetooth low energy protocol.

As used herein, the term "module" can refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term "module" can include memory (shared, dedicated, or group) that stores code executed by the processor.

The term "code," as used above, can include software, firmware, and/or microcode, and can refer to programs, routines, functions, classes, and/or objects. The term "shared," as used above, means that some or all code from multiple modules can be executed using a single (shared) processor. In addition, some or all code from multiple modules can be stored by a single (shared) memory. The term "group," as used above, means that some or all code from a single module can be executed using a group of processors. In addition, some or all code from a single module can be stored using a group of memories.

The apparatuses and methods described herein can be implemented by one or more computer programs executed by one or more processors. The computer programs include processor-executable instructions that are stored on a non-transitory, tangible, computer readable medium. The computer programs can also include stored data. Examples of the non-transitory, tangible, computer readable medium include, but are not limited to, nonvolatile memory, volatile memory, magnetic storage, and optical storage.

The description is merely illustrative in nature and is in no way intended to limit the disclosure, its application, or uses. For purposes of clarity, the same reference numbers may be used in the drawings to identify similar elements. As used herein, the phrase at least one of A, B, and C should be construed to mean a logical (A or B or C), using a non-exclusive logical or. It should be understood that steps within a method can be executed in different order without altering the principles of the present disclosure.

The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

What is claimed is:

1. A method performed by a medical device for transmitting data packets using a communication protocol defined in accordance with the Bluetooth low energy protocol, the method comprising:
   removing select data fields from a data packet defined in accordance with IEEE standard 11073-20601 to form a modified data packet;
   determining a length of the modified data packet;
   determining whether the length of the modified data packet is greater than a predetermined maximum length of data packets under the Bluetooth low energy protocol, as defined in Bluetooth Core Specification version 4.0;
   when the length of the modified data packet is greater than the predetermined maximum length of data packets defined under the Bluetooth low energy protocol, partitioning the modified data packet into a plurality of individual data packets, wherein each of the individual data packets includes a portion of the modified data packet; and
   transmitting the individual data packets via an antenna in accordance with the Bluetooth low energy protocol.

2. The method of claim 1 wherein the select data fields includes a header field.

3. The method of claim 1 wherein removing select data fields from the data packet defined in accordance with IEEE standard 11073 includes removing a data field that includes error detecting code data.

4. The method of claim 3 further comprising:
   calculating new error correcting code data after the removal of the select data fields; and
   storing the new error correcting code data in the modified data packet.

5. The method of claim 3 wherein the error detecting code data includes data for a cyclical redundancy check.

6. The method of claim 1 further comprising:
   determining a total number of individual data packets based on the length of the modified data packet and the predetermined maximum length of data packets defined under the Bluetooth low energy protocol; and
   partitioning the modified data packet into the total number of individual data packets.

7. The method of claim 6 further comprising determining the total number of individual data packets by dividing the length of the modified packet by the predetermined maximum length and rounding the result up to the nearest integer.

8. The method of claim 6 wherein partitioning the modified data packet further comprises appending each of the plurality of individual data packets with an indicator of the total number of individual data packets and a transmission order indicator.

9. The method of claim 1 further comprising leaving data from other, non-removed fields of the data packet defined in accordance with IEEE standard 11073 unchanged to form the modified data packet.

10. The method of claim 1 wherein the data packet includes code for commanding another medical device to perform a function.

11. The method of claim 1 wherein the data packet includes one or more measurements taken by the medical device.

12. The method of claim 1 wherein the data packet includes code for a response to a command received from another medical device.

13. The method of claim 1 further comprising, when the length of the modified data packet is less than the predetermined maximum length of data packets under the Bluetooth low energy protocol, transmitting the modified data packet.

14. A method performed by a medical device for transmitting data packets using a communication protocol defined in accordance with the Bluetooth low energy protocol, the method comprising:
   removing a header field and at least one other data field from a data packet defined in accordance with IEEE standard 11073-20601 to form a modified data packet, the data packet including one of:
      code for commanding another medical device to perform a function;
      one or more measurements taken by the medical device; and
      code for a response to a command received from another medical device;
   leaving data from other, non-removed fields of the data packet defined in accordance with IEEE standard 11073-20601 unchanged to form the modified data packet;
   determining a length of the modified data packet;
   determining whether the length of the modified data packet is greater than a predetermined maximum length of data packets under the Bluetooth low energy protocol, as defined in Bluetooth Core Specification version 4.0;
   determining a total number of individual data packets based on the length of the modified data packet and the predetermined maximum length of data packets;
   when the length of the modified data packet is greater than the predetermined maximum length of data packets defined under the Bluetooth low energy protocol, partitioning the modified data packet into N individual data packets, wherein each of the N individual data packets includes a portion of the modified data packet and N is equal to the total number of individual data packets; and
   transmitting the N individual data packets via an antenna in accordance with the Bluetooth low energy protocol.

15. The method of claim 14 wherein removing at least one other data field from the data packet defined in accordance with IEEE standard 11073-20601 includes removing a data field that includes error detecting code data, and the method further comprising:
   calculating new error correcting code data after the removal of the header field and the at least one other data field; and
   storing the new error correcting code data in the modified data packet.

16. The method of claim 15 wherein the error detecting code data includes data for a cyclical redundancy check.

17. The method of claim 14 further comprising determining the total number of individual data packets by dividing the length of the modified packet by the predetermined maximum length and rounding the result up to the nearest integer.

18. The method of claim 14 wherein partitioning the modified data packet further comprises appending each of the plurality of individual data packets with an indicator of the total number of individual data packets and a transmission order indicator.

19. A medical device for transmitting data packets using a communication protocol defined in accordance with the Bluetooth low energy protocol, the medical device comprising:
  a processor module that removes select data fields from a data packet defined in accordance with IEEE standard 11073-20601 to form a modified data packet, that determines a length of the modified data packet and that, when the length of the modified data packet is greater than a predetermined maximum length of data packets under the Bluetooth low energy protocol as defined in Bluetooth Core Specification version 4.0, partitions the modified data packet into a plurality of individual data packets, where each of the individual data packets includes a portion of the modified data packet; and
  a transceiver that transmits the individual data packets via an antenna in accordance with the Bluetooth low energy protocol.

* * * * *